United States Patent
Jonczyk et al.

(12) 
(10) Patent No.: US 6,169,072 B1
(45) Date of Patent: *Jan. 2, 2001

(54) CYCLIC ADHESION INHIBITORS

(75) Inventors: Alfred Jonczyk, Darmstadt; Günter Hölzemann, Seeheim-Jugenheim, both of (DE); Brunhilde Felding-Habermann, La Jolla, CA (US); Friedrich Rippmann, Heidelberg (DE); Beate Diefenbach, Darmstadt (DE); Horst Kessler, Schwalbach (DE); Roland Haubner; Jochen Wermuth, both of Garching (DE)

(73) Assignee: Merck Patent Gesellschaft Mit (DE)

( * ) Notice: Under 35 U.S.C. 154(b), the term of this patent shall be extended for 0 days.

This patent is subject to a terminal disclaimer.

(21) Appl. No.: 09/164,585

(22) Filed: Oct. 1, 1998

Related U.S. Application Data

(63) Continuation of application No. 08/616,770, filed on Mar. 15, 1996, now Pat. No. 5,849,692, which is a continuation of application No. 08/220,858, filed on Mar. 31, 1994, now abandoned.

(30) Foreign Application Priority Data

Apr. 1, 1993 (DE) .................................................. 43 10 643

(51) Int. Cl.$^7$ .......................... A61K 38/00; A61K 38/12; A61K 38/08; C07K 7/64
(52) U.S. Cl. .................................. 514/11; 514/2; 514/3; 530/317
(58) Field of Search ........................................... 514/2, 17

(56) References Cited

U.S. PATENT DOCUMENTS

| | | | |
|---|---|---|---|
| 4,472,305 | 9/1984 | Hansen et al. | 530/327 |
| 5,192,746 | * 3/1993 | Lobl et al. | 514/11 |
| 5,561,112 | * 10/1996 | Kottrisch et al. | 514/19 |
| 5,753,230 | * 5/1998 | Brooks et al. | 424/158.1 |

FOREIGN PATENT DOCUMENTS 0 406 428  1/1991  (EP) .
0 578 083  1/1994  (EP) .

OTHER PUBLICATIONS

Atlas of Protein Sequence and Structure, vol. 5. Natl. Biomedical Research Foundation, Washington, p. 96, 1972.*
Database Caplus, DN:113;165041. Saiki et al. Jpn. J. Cancer Res. (1990), 81(6–7), 668–75, Jun. 1990.*
Database Caplus, DN: 115:5932 Nicosia et al. Am. J. Pathol. (1991), 138(4), 829–33, Apr. 1991.*
Cheresh, D. Integrins: Structure, Function, Biological Properties. In: Advances in Molecular and Cell Biology, vol. 6, p. 225–251, Jan. 1993.*
Neubert et al., "Synthese cyclischer under cyclisch–verzweigter . . .", *Pharmazie*, 40(8):532–535, 1985.
Smith et al., "Interaction of Integrins $\alpha_v\beta$hd 3 and Glycoprotein IIB . . .", *J. Biol. Chem.*, 265, 12267–12271, 1990.
Aumailley et al., *FEBS*, 291 (1): 50–54, 1991.
Kumagai et al., *Biochemical & Biophyscial Res. Com.*, 177(1), 1991.
The Merck Manual of Diagnosis & Therapy, 11th Ed., pp. 1055–1059, 1966.
Mueller et al., *Angw. Chem. Int. Ed.*, 31(3):326–328, 1992.
Chemical Abstracts, 119(5):49882d (Aug. 2, 1993).
Chemical Abstracts, 118(17);169613t (Apr. 26, 1993).

* cited by examiner

Primary Examiner—Michael Borin
(74) *Attorney, Agent, or Firm*—Millen, White, Zelano & Branigan, P.C.

(57) ABSTRACT

The invention relates to novel cyclopeptides of the formula I cyclo-(Arg-B-Asp-D-E)    I in which B, D, and E have the meanings defined herein, and their salts. These compounds act as interin inhibitors and can be used, in particular, for the prophylaxis and treatment of disorders of the circulation and in tumor therapy.

10 Claims, No Drawings

CYCLIC ADHESION INHIBITORS

This application is a continuation of Ser. No. 08/616,770, filed Mar. 15, 1996, now U.S. Pat. No. 5,849,692, which is a continuation of Ser. No. 08/220,858, filed Mar. 31, 1994, abandoned.

SUMMARY OF THE INVENTION

The invention relates to novel cyclopeptides of the formula I cyclo-(Arg-B-Asp-D-E)    I in which
- B is Gly, Ala, or —HN—Q—CO—,
- D and E in each case independently of one another are Gly, —HN—Q—CO—, Ala, Asn, Asp, Asp(OR), Arg, Cha, Cys, Gln, Glu, His, Ile, Leu, Lys, Lys(Ac), Lys (AcNH$_2$), Lys(AcSH), Met, Nal, Nle, Orn, Phe, 4-Hal-Phe, Phg, Pro, Pya, Ser, Thr, Tia, Tic, Trp, Tyr or Val, where the said amino acid radicals can also be derivatized,
- R is alkyl having 1–6 C atoms,
- Hal is F, Cl, Br or I,
- Q is alkylene having 1–6 C atoms and
- Ac is alkanoyl having 1–10 C atoms, where, if it is a case of radicals of optically active amino acids and amino acid derivatives, both the D and the L forms are included, and also their physiologically acceptable salts.

Similar compounds are known from Pharmazie 40 (8), 532–5, (1985).

An object of the invention is to find novel compounds having useful properties, in particular those which can be used for the production of medicaments.

It has been found that the compounds of the formula I and their salts have very useful properties. In particular, they act as integrin inhibitors, in which case they particularly inhibit the interactions of $\beta_3$- or $\beta_5$-integrin receptors with ligands. The compounds are particularly effective in the case of the integrins $a_v\beta_3$, $a_v\beta_5$ and $a_{IIb}\beta_3$. This action can be demonstrated, for example, by the method which is described by J. W. Smith et al. in J. Biol. Chem. 265, 12267–12271 (1990). In addition, there are anti-inflammatory effects. All these actions can be demonstrated with the aid of methods which are known from the literature.

It is known that compounds which inhibit or block the $\beta_3$-integrin receptor ligand interactions, such as the binding of fibrinogen to $\beta_3$-integrin receptors (adhesion receptor antagonist or ARA), can be used as therapeutic agents. Furthermore, such compounds also inhibit cell adhesion in the case of the formation of osteoclasts.

Thus, the compounds can be employed as pharmaceutically active compounds in human and veterinary medicine, in particular, for the prophylaxis and the treatment of disorders of the circulation, thrombosis, cardiac infarct, arteriosclerosis, inflammations, apoplexy, angina pectoris, tumor disorders (e.g., melanoma, sarcoma, and epithelioma), osteolytic disorders, in particular, osteoporosis, antiogenesis and restenosis after angioplasty. The compounds may furthermore be employed to improve the healing of wounds.

The compounds are also suitable as antimicrobial agents which avoid infections as caused, for example, by bacteria, fungi or yeasts. The substances are useful as accompanying antimicrobial agents in cases where operations are effected in order to insert non-corporal materials, for example such as biomaterials, implants, catheters or heart-pacemakers. They act as antiseptics.

The abbreviations of amino acid radicals shown above and below stand for the radicals of the following amino acids:

| | |
|---|---|
| Abu | 4-aminobutyric acid |
| Aha | 6-aminohexanoic acid |
| Ala | alanine |
| Asn | asparagine |
| Asp | aspartic acid |
| Asp (OR) | aspartic acid (β-ester) |
| Arg | arginine |
| Cha | 3-cyclohexylalanine |
| Cit | citrulline |
| Cys | cysteine |
| Dab | 2,4-diaminobutyric acid |
| Gln | glutamine |
| Glu | glutamic acid |
| Gly | glycine |
| His | histidine |
| Ile | isoleucine |
| Leu | leucine |
| Lys | lysine |
| Lys (Ac) | N'-alkanoyllysine |
| Lys(AcNH$_2$) | N'-aminoalkanoyllysine |
| Lys(AcSH) | N'-mercaptoalkanoyllysine |
| Met | methionine |
| Nal | 3-(2-naphthyl)-alanine |
| Nle | norleucine |
| Orn | ornithine |
| Phe | phenylalanine |
| 4-Hal-Phe | 4-halogenophenylalanine |
| Phg | phenylglycine |
| Pro | proline |
| Pya | 3-(2-pyridyl)-alanine |
| Ser | serine |
| Tia | 3-(2-thienyl)-alanine |
| Tic | tetrahydroisoquinoline-3-carboxylic acid |
| Thr | threonine |
| Trp | tryptophan |
| Tyr | tyrosine |
| Val | valine. |

In addition, the following have the meanings below:

| | |
|---|---|
| BOC | tert-butoxycarbonyl |
| CBZ | benzyloxycarbonyl |
| DCCI | dicyclohexylcarbodiimide |
| DMF | dimethylformamide |
| EDCI | N-ethyl-N'-(3-dimethylaminopropyl)-carbodiimide hydrochloride |
| Et | ethyl |
| FMOC | 9-fluorenylmethoxycarbonyl |
| HOBt | 1-hydroxybenzotriazole |
| Me | methyl |
| Mtr | 4-methoxy-2,3,6-trimethylphenylsulfonyl |
| OBut | tert-butyl ester |
| OMe | methyl ester |
| OEt | ethyl ester |
| POA | phenoxyacetyl |
| TBTU | 2-(1H-benzotriazol-1-yl)-1,1,3,3-tetramethyluronium tetrafluoroborate |
| TFA | trifluoroacetic acid |
| Trt | trityl (triphenylmethyl). |

If the amino acids mentioned above can occur in several enantiomeric forms, then all of these forms and also their mixtures (e.g., the DL-forms) are included above and below, e.g., as constituents of the compounds of the formula I. The amino acids, e.g., as constituents of compounds of the formula I, may furthermore be provided with appropriate protective groups known per se.

Derivatized amino acid radicals are, for example, those radicals which are protected by one of the hydroxy or amino protecting groups discussed below. Preferred protecting groups are, for example, Boc and Fmoc for the N-terminus and OMe and OEt for the C-terminus of the amino acid radicals. Furthermore, if an amino acid residue has a functional group in its side chain, this group could be derivatized, too. The following are examples of derivatized amino acids: Ala(2-thienyl); 4-NO$_2$—Phe; Lys(Aha); Asp(OEt); Lys (BOC-Aha); Tyr(OEt); Arg(Mtr); Asn(Trt); Asp(OBut); Cys (Trt); Cys(SBut); Glu(OBut); Gln(Trt); His(Trt); Lys(BOC); Ser(But); Thr(But); Tyr(But); Lys(AcH); Lys(AcNH$_2$); and Lys(AcSH), wherein Ac is —CO—C$_n$H$_{2n}$— (n=2–12).

The invention further relates to a process for the preparation of a compound of the formula I or one of its salts, characterized in that it is liberated from one of its functional derivatives by treating with a solvolyzing or hydrogenolyzing agent, or in that a peptide of the formula II

   II in which
Z is
  -Arg-B-Asp-D-E,
  B-Asp-D-E-Arg-,
  -Asp-D-E-Arg-B-,
  -D-E-Arg-B-Asp, or
  -E-Arg-B-Asp-D, or a reactive derivative of such a peptide is treated with a cyclizing agent [e.g., dicyclohexylcarbodiimide (DCCI), N-ethyl-N'-(3-dimethylaminopropyl)-carbodiimide (EDCI), benzyltriazolyltetramethyluronium-tetrafluoroborate (TBTU), and diisopropylcarbodiimide (DICI)]. and/or in that a basic or acidic compound of the formula I is converted into one of its salts by treating with an acid or base.

The radicals B, D, E and Z above and below have the meanings given in the formulae I and II, if not expressly stated otherwise.

In the above formulae, alkyl is preferably methyl, ethyl, isopropyl or tert-butyl.

The group B is preferably Gly, but also —NH—(CH$_2$)$_2$—CO—, —NH—(CH$_2$)$_3$—CO—, —NH—(CH$_2$)$_5$—CO— or Ala. D is preferably Phe, in particular D-Phe, but also 4-Hal-Phe, particularly 4-I-Phe, and Pro, Tic, Lys, Nal or Phg, the D forms being particularly preferred.

Accordingly, the invention is particular relates to those compounds of the formula I in which at least one of the radicals has one of the preferred meanings given above.

A preferred group of compounds can be expressed by the part formula Ia, which otherwise corresponds to the formula I, but in which
  B is Gly, —NH—(CH$_2$)$_2$—CO—, —NH—(CH$_2$)$_3$—CO—, —NH—(CH$_2$)$_5$—CO— or Ala
  D is D-Pro, D-Tic, Phe, D-Nal, D-Phg or 4-I-Phe and
  E is Val, Lys, Gly, Ala, Phe, Leu, Lys(Ac) or Nle.

A further preferred group of compounds can be expressed by the part formula Ib, which otherwise corresponds to the formula I, but in which
  B is Gly
  D is D-Phe and
  E is Val, Lys or Gly.

The compounds of the formula I and also the starting materials for their preparation are otherwise prepared by known methods, as are described in the literature (e.g., in the standard works such as Houben-Weyl, Methoden der organischen Chemie, (Methods of Organic Chemistry) Georg-Thieme-Verlag, Stuttgart), in particular under reaction conditions which are known and suitable for the reactions. In this context, use can also be made of known variants which are not mentioned in more detail here.

The starting substances can also be formed in situ, if desired, such that they are not isolated from the reaction mixture, but immediately reacted further to give the compounds of the formula I.

The compounds of the formula I can be obtained by liberating them from their functional derivatives by solvolysis, in particular hydrolysis, or by hydrogenolysis.

Preferred starting materials for the solvolysis or hydrogenolysis are those which contain appropriate protected amino and/or hydroxyl groups instead of one or more free amino and/or hydroxyl groups, preferably those which carry in amino protecting group instead of an H atom which is bonded to an N atom, e.g., those which correspond to the formula I, but contain an NHR' group (in which R' is an amino protecting group, e.g., BOC or CBZ) instead of an NH$_2$ group.

In addition, starting materials are preferred which carry a hydroxyl protecting group instead of the H atom of a hydroxyl group, e.g., those which correspond to the formula I, but contain an R"O-phenyl group (in which R" is a hydroxyl protecting group) instead of a hydroxyphenyl group.

Several—identical or different—protected amino and/or hydroxyl groups can be present in the molecule of the starting material. If the protective groups present are different from one another, in many cases they can be removed selectively.

The expression "amino protecting group" is generally known and relates to groups which are suitable for protecting (for blocking) an amino group from chemical reactions, but which are easily removeable, after the desired chemical reaction has been carried out at other positions in the molecule. Typical groups of this type are, in particular, unsubstituted or substituted acyl, aryl, aralkoxymethyl or aralkyl groups. As the amino protecting groups are removed after the desired reaction (or reaction sequence), their nature and size is otherwise not critical; but those having 1–20, in particular 1–8, C atoms are preferred. The expression "acyl group" is to be taken in its widest sense in connection with the present process. It includes acyl groups derived from aliphatic, araliphatic, aromatic or heterocyclic carboxylic acids or sulfonic acids and in particular alkoxycarbonyl, aryloxycarbonyl and, above all, aralkoxycarbonyl groups. Examples of acyl groups of this type are alkanoyl such as acetyl, propionyl or butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxybenzyloxycarbonyl, Fmoc, and arylsulfonyl such as Mtr. Preferred amino protecting groups are BOC and Mtr, and in addition CBZ, Fmoc, benzyl and acetyl.

The expression "hydroxy protecting groups" is also generally known and relates to groups which are suitable for protecting a hydroxyl group from chemical reactions, but which are easily removable, after the desired chemical reaction has been carried out at other positions in the molecule. Typical groups of this type are the abovementioned unsubstituted or substituted aryl, aralkyl or acyl groups, and in addition also alkyl groups. The nature and size of the hydroxy protecting groups is not critical, as they are removed again after the desired chemical reaction or reaction sequence; preferred groups are those having 1–20, in particular 1–10 C atoms. Examples of hydroxyl protecting groups are, inter alia, benzyl, p-nitrobenzoyl, p-toluenesulfonyl, tert-butyl and acetyl, benzyl and tert-butyl being particularly preferred. The COOH groups in aspartic acid and glutamic acid are preferably protected in the form of their tert-butyl esters (e.g., Asp (OBut)).

The functional derivatives of the compounds of the formula I to be used as starting materials can be prepared by customary methods of amino acid and peptide synthesis, such as are described, e.g., in the standard works and patent applications mentioned, and, e.g., also by the Merrifield solid phase method (B. F. Gysin and R. B. Merrifield, J. Am. Chem. Soc. 94, 3102 et seq. (1972)).

The liberation of the compounds of the formula I from their functional derivatives is carried out—depending on the protecting group used—e.g., with strong acids, preferably with TFA or perchloric acid, but also with other strong inorganic acids such as hydrochloric acid or sulfuric acid, or strong organic carboxylic acids such as trichloroacetic acid or sulfonic acids such as benzene- or p-toluenesulfonic acid. The presence of an additional inert solvent is possible, but not always necessary. Suitable inert solvents are preferably organic, for example carboxylic acids such as acetic acid, ethers such as tetrahydrofuran or dioxane, amides such as DMF, halogenated hydrocarbons such as dichloromethane, and in addition also alcohols such as methanol, ethanol or isopropanol and also water.

In addition, mixtures of this abovementioned solvents are suitable. TFA is preferably used in an excess without addition of a further solvent, perchloric acid in the form of a mixture of acetic acid and 70% perchloric acid in the ratio 9:1. The reaction temperatures for the cleavage are preferably about 0–50°, preferably 15–30° (room temperature).

The groups BOC, OBut and Mtr can be removed, e.g., preferably using TFA in dichloromethane or with about 3 to 5 N HCl in dioxane at preferably about 15–30°, the Fmoc group using an about 5- to 50% solution of dimethylamine, diethylamine or piperidine in DMF at preferably about 15–30°.

Protecting groups which can be removed by hydrogenolysis (e.g. CBZ or benzyl) can be removed, e.g., by treating with hydrogen in the presence of a catalyst (e.g. a noble metal catalyst such as palladium, preferably on a carrier such as carbon). Suitable solvents in this case are those mentioned above, in particular, e.g., alcohols such as methanol or ethanol or amides such as DMF. The hydrogenolysis is carried out, as a rule, at temperatures of preferably about 0–100° and pressures of preferably about 1–200 bar, especially at 20–30° and 1–10 bar. Hydrogenolysis of the CBZ group is easily carried out, e.g., on 5 to 10% Pd—C in methanol or using ammonium formate (instead of $H_2$) on Pd—C in methanol/DMF at preferably bout 20–30°.

Compounds of the formula I can also be obtained by cyclization of compounds of the formula II under the conditions of a peptide synthesis. In this case, the reaction is preferably carried out by customary methods of peptide synthesis, as are described, e.g., in Houben-Weyl, loc cit. volume 15/II, pages 1 to 806 (1974).

The reaction is preferably carried out in the presence of a dehydrating agent, e.g., a carbodiimide such as DCCI or EDCI, and in addition propanephosphonic anhydride (compare Angew. Chem. 92, 129 (1980)), diphenylphosphoryl azide or 2-ethoxy-N-ethoxycarbonyl-1,2-dihydroquinoline, in an inert solvent, e.g., a halogenated hydrocarbon such as dichloromethane, an ether such as tetrahydrofuran or dioxane, an amide such as DMF or dimethylacetamide, a nitrile such as acetonitrile, or in mixtures of these solvents, at temperatures of preferably about −10–40, especially 0–30°. In order to promote intramolecular cyclization before intermolecular peptide bonding, it is preferable to work in dilute solutions (dilution principle).

Instead of II, suitable reactive derivatives of these substances can also be employed in the reaction, e.g., those in which reactive groups are intermediately blocked by protecting groups. The amino acid derivatives II can be used, e.g., in the form of their activated esters which are preferably formed in situ, e.g., by addition of HOBt or N-hydroxysuccinimide.

The starting materials of the formula II are, as a rule, novel. They can be prepared by known methods, e.g., the abovementioned methods of peptide synthesis and of removal of protective groups.

As a rule, protected pentapeptide esters of the formula R'—Z—OR", e.g., BOC-Z-OMe or BOC-Z-OEt, are initially synthesized, which are first hydrolyzed to give acids of the formula R'—Z—OH, e.g., BOC-Z-OH; the protective group R' is removed from these, by means of which the free peptides of the formula H—Z—OH (II) are obtained.

A base of the formula I can be converted into the appropriate acid addition salt using an acid. Suitable acids for this reaction are in particular those which yield physiologically acceptable salts. Inorganic acids can thus be used, e.g., sulfuric acid, nitric acid, hydrohalic acids such as hydrochloric acid or hydrobromic acid, phosphoric acids such as orthophosphoric acid and sulfamic acid, and in addition organic acids, in particular aliphatic, alicyclic, araliphatic, aromatic or heterocyclic mono- or polybasic carboxylic, sulfonic or sulfuric acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicyclic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids, and laurylsulfuric acid. Salts with physiologically unacceptable acids, e.g., picrates, can be used for the isolation and/or purification of the compounds of the formula I.

On the other hand, an acid of the formula I can be converted into one of its physiologically acceptable metal or ammonium salts by reaction with a base. Suitable salts here are in particular the sodium, potassium, magnesium, calcium and ammonium salts, and also substituted ammonium salts, e.g., the dimethyl-, diethyl- or diisopropylammonium salts, monoethanol-, diethyanol- or triethanolammonium salts, cyclohexyl- or dicyclohexylammonium salts, dibenzylethylenediammonium salts, and furthermore, e.g., salts with N-methyl-D-glucamine or with arginine or lysine.

The novel compounds of the formula I and their physiologically acceptable salts can be used for the production of pharmaceutical preparations by bringing them into a suitable dosage form together with at least one excipient or auxiliary and, if desired, together with one or more other active compound(s). The preparations thus obtained can be employed as medicaments in human or veterinary medicine. Suitable excipient substances are organic or inorganic substances which are suitable for enteral (e.g., oral or rectal), parenteral (e.g., intravenous injection) or local (e.g., topical, dermal, ophthalmic or nasal) administration or for administration in the form of an inhalant spray and which do not react with the novel compounds, for example water or aqueous isotonic a saline solution, lower alcohols, vegetable oils, benzyl alcohols, polyethylene glycols, glycerol triacetate and other fatty acid glycerides, gelatin, soya lecithin, carbohydrates such as lactose or starch, magnesium stearate, talc, cellulose and petroleum jelly. Tablets, coated tablets, capsules, syrups, juices or drops, in particular, are used for oral administration; film tablets and capsules having enteric coatings or capsule shells are especially of interest. Suppositories are used for rectal administration, and solutions, preferably oily or aqueous solutions, and in addition suspension, emulsions or implants, are used for parenteral administration. Solutions, e.g., which can be used in the form of eye drops, and in addition, e.g., suspension, emulsions, creams, ointments or compresses are suitable for topical application. Sprays can be used which contain the active compound either dissolved or suspended in a propellant gas or propellant gas mixture (e.g., $CO_2$ or chlorofluorohyrocarbons) for administration as inhalant sprays. The active compound here is preferably used in micronized form, it being possible for one or more additional physiologically tolerable solvents to be present, e.g., ethanol. Inhalant solutions can be administered with the aid of customary inhalers. The novel compounds can also be lyophilized and the lyophilizates obtained used, e.g., for the production of injection preparations. The injections can be administered as a bolus or as a continuous infusion (e.g., intravenous, intramuscular, subcutaneous or intrathecal). The preparations indicted can be sterilized and/or can contain auxiliaries such as preservatives, stabilizers and/or wetting agents, emulsifiers, salts for influencing osmotic pressure, buffer substances, colorants and/or flavorings. If desired, they can also contain one or more other active compounds, e.g., one or more vitamins.

The substances according to the invention can as a rule be administered in analogy to other known commercially available peptides, but in particular in analogy to the compounds described in U.S. Pat. No. 4,472,305, preferably in dosages of about 0.05–500, in particular, 0.5–100 mg per dosage unit. The daily dose is preferably about 0.01–2 mg/kg of body weight. The specific dose for each intended patient depends, however, on many different factors, for example the activity of the specific compound employed, the age, body weight, general state of health, sex, the diet, the time and route of administration, and the rate of excretion, pharmaceutical combination and severity of the particular disorder to which the therapy applies. Parenteral administration is preferred.

Suitable preparations for using the compounds as antimicrobial agents are, for example, injection vials, ampoules, solutions, and capsules. Carriers, excipients, and further additives are mentioned in Examples A–H. The amount of the inventive compound in the antimicrobial agents is preferably about 0.05–500 mg per dosage unit.

In addition, the novel compounds of the formula I can be used as integrin ligands for the preparation of columns for affinity chromatography to be used in the preparation of integrins in pure form.

The ligand, i.e., a peptide derivative of the formula I, is in this case covalently coupled to a polymeric support via anchor functions.

To purify integrins, a sample containing integrins and other components is, for example, introduced into a chromatographic column containing a polymeric support material to which ligands, i.e., compounds of formula I, are covalently coupled, for example, via an anchor function. Integrins within the sample bind to the ligands and are thereby separated from the sample. The chromatographic column can then be treated with a peptide solution, a salt gradient, or another substance, for example, EDTA, which is a better ligand than the peptide in order to separate the integrins.

Suitable polymeric support materials are the polymeric solid phases known per se in peptide chemistry, having preferably hydrophilic properties, for example crosslinked polysugars, such as cellulose, Sepharose or Sephadex®, acrylamides, polymers based on polyethylene glycol or Tentakel polymers®.

Suitable anchor functions which are linked to the polymeric supports are preferably linear alkylene chains having 2–12 C atoms, which are bonded directly to the polymer at one end and have a functional group, such as, e.g., hydroxyl, amino, mercapto, maleimideo, or —COOH, at the other end and are suitable to be linked to a functional section, preferably in one of the side chains, of the respective peptide.

It is possible in this case that the peptide be bonded directly or likewise via a second anchor function to the anchor function of the polymer. It is also possible that peptides which contain amino acid radicals with functionalized side chains are bonded to the anchor function of the polymer via these.

Moreover, certain amino acid radicals which are a constituent of the peptides of the formula I can be modified in their side chains in such a way that they are available for anchorage via, e.g., SH, OH, $NH_2$ or COOH groups with the anchor of the polymer.

In this connection, unusual amino acids are possible, such as, e.g., phenylalanine derivatives which carry a mercapto, hydroxyl, amino or carboxyalkyl chain in position 4 of the phenyl ring, the functional group being located at the end of the chain.

Examples of amino acid radicals whose side chain can be used directly as an anchor function are e.g. Lys, Orn, Art, Dab, Asp, Asn, Glu, Gln, Ser, Thr, Cys, Cit or Tyr.

Thus, for example, the polymeric support and the peptide suitable as an integrin ligand can each have an anchor function. Both anchors can then be connected via their functional groups at the end of each anchor molecule. In some cases, where amino acid radicals have a side chain with a functional group, this side chain can serve as an anchor and is connected directly to the anchor of the polymeric support.

Examples of N-terminal anchors are radicals such as, e.g., —CO—$C_nH_{2n}$—$NH_2$, —CO—$C_nH_{2n}$—OH, —CO—$C_nH_{2n}$—SH or —CO—$C_nH_{2n}$—COOH, where n=2–12, the length of the alkylene chain not being critical and it optionally also being possible to replace this, e.g., by appropriate aryl or alkylaryl radicals.

C-terminal anchors can be, for example, —O—$C_nH_{2n}$—SH, —O—$C_nH_{2n}$—OH, —O—$C_nH_{2n}$—$NH_2$, —O—$C_nH_{2n}$—COOH, —NH—$C_nH_{2n}$—SH, —NH—$C_nH_{2n}$—OH, —NH—$C_nH_{2n}$—$NH_2$ or —NH—$C_nH_{2n}$—COOH, what has already been said in the preceding section applying to n and also to the alkylene chain.

The N- and C-terminal anchors can also be used as anchor components for an already functionalized side chain of an amino acid radical. Suitable amino acid radicals here, for example, are those such as Lys(CO—$C_5H_{10}$—$NH_2$), Asp (NH—$C_3H_6$—COOH) or Cys($C_3H_6$—$NH_2$), the anchor always being bonded to the functional group of the side chain.

The preparation of the materials for affinity chromatography for purifying integrins is carried out under conditions such as are customary for the condensation of amino acids and are known per se and have already been outlined in the section for the preparation of the compounds of the formula I.

All temperatures above and below are stated in ° C. In the following examples, "customary working up" means: water is added, if necessary, the mixture is neutralized and extracted with ether or dichloromethane, the organic phase is separated off, dried over sodium sulfate, filtered and evaporated and the residue is purified by chromatography on silica gel and/or crystallization. RT=retention time (minutes) for HPLC on a Lichrosorb RP select B (250–4.7 µm) column, eluent: 0.3% TFA in water; isopropanol gradient of 0–80 vol % in 50 min at 1 ml/min. Flow and detection at 215 nm. $M^+$=molecular peak in the mass spectrum, obtained by the fast atom bombardment method.

Without further elaboration, it is believed that using the preceding description, one skilled in the art can utilize the present invention to its fullest extent. The following preferred specific embodiments are, therefore, to be construes as merely illustrative and not limitative of the remainder of the disclosure in any way whatsoever.

In the foregoing and in the following examples, all temperatures are set forth uncorrected in degrees Celsius; and unless otherwise indicated, all parts and percentages are by weight.

The entire disclosures of all applications, patents, and publications cited herein and of corresponding German P 43 10 643.9, filed Apr. 1, 1993, are hereby incorporated by reference.

EXAMPLES

Example 1

A solution of 0.2 g of H-Arg-Gly-Asp-D-Pro-Val-Ona [e.g., obtainable from Fmoc-Arg-Gly-Asp-D-Pro-Val-O-Wang, -O-Wang being the radical of a 4-oxymethylphenoxymethyl polystyrene resin used in the modified Merrifield techniques, by removal of the Fmoc group with piperidine/DMF and removal of the resin with TFA/$CH_2Cl_2$ (1:1] in 15 ml of DMF is diluted with 85 ml of dichloromethane and is treated with 50 mg of $NaHCO_3$. After cooling in a dry ice/acetone mixture, 40 µl of diphenylphosphoryl azide are added. After standing at room temperature for 16 hours, the solution is concentrated. The concentrate is gel filtered (Sephadex G10 column in isopropanol/water 8:2) and then purified by means of HPLC in the customary manner. Cyclo-(Arg-Gly-Asp-D-Pro-Val) is obtained; RT=13.4; $M^+$ 525.

The following are obtained analogously by cyclization of the corresponding linear peptides:

cyclo-(Arg-Gly-Asp-D-Tic-Val); RT=18.4; $M^+$ 587;
cyclo-(Arg-Gly-Asp-D-Phe-Val); $M^+$ 575;
cyclo-(Arg-Gly-Asp-D-Lys-Val); RT=6.8; $M^+$ 556;
cyclo-(Arg-Gly-Asp-D-Phe-Lys); RT=10.9; $M^+$ 604;
cyclo-(Arg-Gly-Asp-D-Phe-Gly); RT=13.1; $M^+$ 533;
cyclo-(Arg-Gly-Asp-D-Phe-Ala); RT=14.3; $M^+$ 547;
cyclo-(Arg-Gly-Asp-D-Phe-Phe); RT=22.0; $M^+$ 623;
cyclo-(Arg-Gly-Asp-D-Phe-Leu); RT=21.2; $M^+$ 589;
cyclo-(Arg-Gly-Asp-D-Nal-Val); RT=24.7; $M^+$ 625;
cyclo-(Arg-Gly-Asp-D-Phg-Val); RT=16.5; $M^+$ 561;
cyclo-(Arg-Gly-Asp-Phe-Gly); RT=13.2; $M^+$ 533 (SEQ ID NO:1);
cyclo-(Arg-Gly-Asp-Phe-D-Ala); RT=14.8; $M^+$ 547;
cyclo-(Arg-Gly-Asp-Phe-D-Phe); RT=20.2; $M^+$ 623;
cyclo-(Arg-Gly-Asp-Phe-D-Leu); RT=21.4; $M^+$ 589;
cyclo-(Arg(Mtr)-Gly-Asp-D-Phe-Lys); RT=23.4; $M^+$ 816;
cyclo-(Arg-Gly-Asp-D-Phe-Lys($H_3C$—CO); RT=17.0; $M^+$ 646;
cyclo-(Arg(Mtr)-β-Ala-Asp-Phe-D-Val); RT=28.2; $M^+$ 801;
cyclo-(Arg-Gly-Asp-D-Phe-Nle); RT=22.0; $M^+$ 589;
cyclo-(D-Arg-Gly-D-Asp-D-Phe-Val); RT=17.5; $M^+$ 575;
cyclo-(Arg-Gly-D-Asp-D-Phe-D-Gly); RT=18.7; $M^+$ 575;
cyclo-(Arg-D-Ala-Asp-D-Phe-Val); RT=18.9; $M^+$ 589;
cyclo-(Arg-D-Ala-Asp-Phe-D-Val); RT=19.1; $M^+$ 589 (SEQ ID NO:2);
cyclo-(Arg-Aha-Asp-D-Phe-Val); RT=20.8; $M^+$ 631;
cyclo-(Arg-Abu-Asp-Phe-D-Val); RT=17.2; $M^+$ 603;
cyclo-(Arg-Aha-Asp-Phe-D-Val); RT=19.8; $M^+$ 631;
cyclo-(Arg-Abu-Asp-D-Phe-Val); RT=17.8; $M^+$ 603;
cyclo-(Arg-Gly-Asp-D-(4-I-Phe)-Val); RT=23.3; $M^+$ 701;
cyclo-(Arg-Gly-Asp-Phe-Val); RT=21.8; $M^+$ 575;
cyclo-(Arg-Gly-D-Asp-D-Phe-Val); RT=20.7; $M^+$ 575;
cyclo-(D-Arg-Gly-Asp-Phe-D-Val); RT=20.8; $M^+$ 575;
cyclo-(D-Arg-Gly-Asp-D-Phe-Val); RT=21.9; $M^+$ 575;
cyclo-(Arg-Gly-D-Asp-D-Phe-Val); RT=20.7; $M^+$ 575;
cyclo-(Arg-Gly-Asp-Phe-D-Nal);
cyclo-(Arg-Gly-Asp-Phe-D-Leu);
cyclo-(Arg-Gly-Asp-Phe-D-Ser);
cyclo-(Arg-Gly-Asp-D-Nal-Leu);
cyclo-(Arg-Gly-Asp-Nal-D-Val);
cyclo-(Arg-Gly-Asp-Phg-D-Val);
cyclo-(Arg-Gly-Asp-Trp-D-Val);
cyclo-(Arg-Gly-Asp-Ala(2-thienyl)-D-Val);
cyclo-(Arg-Gly-Asp-Lys-D-Val);
cyclo-(Arg-Gly-Asp-(4-$NO_2$-Phe)-D-Val);
cyclo-(Arg-Gly-Asp-Cha-D-Val);
cyclo-(Arg-Gly-Asp-D-Phe-β-Ala);
cyclo-(Arg-Gly-Asp-D-Phe-Abu);
cyclo-(Arg-Gly-Asp-D-Phe-Aha);
cyclo-(Arg-Gly-Asp-D-Phe-Lys);
cyclo-(Arg-Gly-Asp-D-Phe-Pro);
cyclo-(Arg-Gly-Asp-D-Phe-Arg);
cyclo-(Arg-Gly-Asp-D-Phe-Lys(Aha));
cyclo-(Arg-Gly-Asp-D-Phe-Nal);
cyclo-(Arg-Gly-Asp-D-Phe-Ser);
cyclo-(D-Arg(Mtr)-Gly-Asp(OBut)-D-Phe-Val);
cyclo-(Arg(Mtr)-Gly-D-Asp(OEt)-D-Phe-Val);
cyclo-(Arg(Mtr)-Gly-Asp-Phe-D-Nal);
cyclo-(Arg(Mtr)-Gly-Asp-Phe-D-Leu);
cyclo-(Arg(Mtr)-Gly-Asp-Phe-D-Ser);
cyclo-(Arg(Mtr)-Gly-Asp-D-Nal-Leu);
cyclo-(Arg(Mtr)-Gly-Asp-Nal-D-Val);
cyclo-(Arg(Mtr)-Gly-Asp-Phg-D-Val);
cyclo-(Arg(Mtr)-Gly-Asp-Trp-D-Val);
cyclo-(Arg-Gly-Asp-D-Phe-Lys(Boc-Aha);
cyclo-(Arg-Gly-Asp-D-Phe-Lys(CO—$CH_2SH$));
cyclo-(Arg-Gly-Asp-D-Phe-Lys(CO—$(CH_2)_2SH$));
cyclo-(Arg-Gly-Asp-D-Phe-Lys(CO—$(CH_2)_3SH$));

cyclo-(Arg-Gly-Asp-D-Phe-Lys(CO—(CH$_2$)$_4$SH));
cyclo-(Arg-Gly-Asp-D-Phe-Lys(CO—(CH$_2$)$_5$SH));
cyclo-(Arg-Gly-Asp-D-Tyr-Val);
cyclo-(Arg-Gly-Asp-D-(4-Cl—Phe)-Val);
cyclo-(Arg-Gly-Asp-D-Pya-Val);
cyclo-(Arg-Gly-Asp-D-NMe-Phe-Val);
cyclo-(Arg-Gly-Asp-D-Tyr(OEt)-Val);
cyclo-(Arg-Gly-Asp-D-Arg-Val);
cyclo-(Arg-Gly-Asp-D-Trp-Val);
cyclo-(Arg-Gly-Asp-D-Ala(2-thienyl)-Val);
cyclo-(Arg-Gly-Asp-D-Tyr-NMe-Val);
cyclo-(Arg-Gly-D-Asp-D-Phe-Val);
cyclo-(Arg-Gly-D-Asp-Phe-D-Val);
cyclo-(D-Arg-Gly-Asp-Phe-D-Val);
cyclo-(D-Arg-Gly-D-Asp-Phe-Val).

Example 2

A solution of 0.28 g of cyclo-(Arg(Mtr)-β-Ala-Asp-Phe-D-Val) [obtainable by cyclization according to Ex. 1] in 8.4 ml of TFA, 1.7 ml of dichloromethane and 0.9 ml of thiophenol is allowed to stand at room temperature for 4 hours, then concentrated and, after diluting with water, freeze-dried. Gel filtration on Sephadex G 10 (acetic acid/water 1:1) and subsequent purification by preparative HPLC under the conditions indicated give cyclo-(Arg-β-Ala-Asp-Phe-D-Val); RT=17.0; M$^+$ 589.

The following are obtained analogously:
from cyclo-(Arg(Mtr)-Gly-Asp-D-Phe-Lys:
  cyclo-(Arg-Gly-Asp-D-Phe-Lys); RT=10.9; M$^+$ 604
from cyclo-(D-Arg(Mtr)-Gly-Asp(OBut)-D-Phe-Val):
  cyclo-(D-Arg-Gly-Asp-D-Phe-Val);
from cyclo-(Arg(Mtr)-Gly-D-Asp(OEt)-D-Phe-Val):
  cyclo-(Arg-Gly-D-Asp-D-Phe-Val);
from cyclo-(Arg(Mtr)-Gly-Asp-Phe-D-Nal):
  cyclo-(Arg-Gly-Asp-Phe-D-Nal);
from cyclo-(Arg(Mtr)-Gly-Asp-Phe-D-Leu):
  cyclo-(Arg-Gly-Asp-Phe-D-Leu);
from cyclo-(Arg(Mtr)-Gly-Asp-Phe-D-Ser):
  cyclo-(Arg-Gly-Asp-Phe-D-Ser);
from cyclo-(Arg(Mtr)-Gly-Asp-D-Nal-Leu):
  cyclo-(Arg-Gly-Asp-D-Nal-Leu);
from cyclo-(Arg(Mtr)-Gly-Asp-Nal-D-Val):
  cyclo-(Arg-Gly-Asp-Nal-D-Val);
from cyclo-(Arg(Mtr)-Gly-Asp-Phg-D-Val):
  cyclo-(Arg-Gly-Asp-Phg-D-Val);
from cyclo-(Arg(Mtr)-Gly-Asp-Trp-D-Val):
  cyclo-(Arg-Gly-Asp-Trp-D-Val).

Example 3

80 mg of cyclo-(Arg-Gly-Asp-D-Phe-Leu) are dissolved in 0.01 M HCl five to six times and freeze-dried after each dissolving operation. Subsequent purification by HPLC gives cyclo-(Arg-Gly-Asp-D-Phe-Leu). HCl; RT=20.6; M$^+$ 589.

The following are obtained analogously
from cyclo-(Arg-Gly-Asp-D-Phe-Val):
  cyclo-(Arg-Gly-Asp-D-Phe-Val). HCl; RT=18.4; M$^+$ 575;
from cyclo-(Arg-Gly-Asp-D-Phe-Leu):
  cyclo-(Arg-Gly-Asp-D-Phe-Leu). HCl;
from cyclo-(Arg-Gly-Asp-D-Phe-Leu) by treatment with acetic acid:
  cyclo-(Arg-Gly-Asp-D-Phe-Leu). H$_3$C—COOH; RT=19.2; M$^+$ 589;
from cyclo-(Arg-Gly-Asp-D-Phe-Leu) by treatment with nitric acid:
  cyclo-(Arg-Gly-Asp-D-Phe-Leu). HNO$_3$; RT=20.4; M$^+$ 589;

Example 4

To prepare affinity phases, 0.9 g of N-maleimido-(CH$_2$)$_5$-CO—NH—(CH$_2$)$_3$-polymer [obtainable by condensation of N-maleimido-(CH$_2$)$_5$-COOH with N$_2$N-(CH$_2$)$_3$-polymer] is suspended in 10 ml of 0.1 m sodium phosphate buffer at pH 7 and 1 equivalent of cyclo-(Arg-Gly-Asp-D-Phe-Lys (CO(CH$_2$)$_2$SH) is added at 4°. The reaction mixture is stirred for 4 hours with simultaneous warming to room temperature, and the solid residue is filtered off and washed twice with 10 ml each of buffer solution (pH 7) and then three times with 10 ml each of water. cyclo-(Arg-Gly-Asp-D-Phe-Lys(CO(CH$_2$)$_2$S-3-(N-maleimido-(CH$_2$)$_5$-CONH—(CH$_2$)$_3$-polymer)) is obtained.

Example 5

Analogously to Example 1, the following polymeric phase is obtained by condensation of polymer-O-(CH$_2$)$_3$—NH$_2$ [commercially available] and cyclo-(Arg-Gly-Asp-D-Pro-Lys(CO(CH$_2$)$_4$COOH) [obtainable by condensation of adipic acid with cyclo-(Arg-Gly-Asp-D-Pro-Lys) under the conditions mentioned]:

cyclo-(Arg-Gly-Asp-D-Pro-Lys-(CO—(CH$_2$)$_4$—CO—NH—(CH$_2$)$_3$—O—polymer)

The following are obtained analogously by condensation of cyclo-(Arg-Gly-Asp-D-Phe-Lys-(CO—(CH$_2$)$_5$—NH$_2$)) with HOOC-CH$_2$—O-polymer:
  cyclo-(Arg-Gly-Asp-D-Phe-Lys-(CO—(CH$_2$)$_5$—NH—CO—CH$_2$—O-polymer)).

The examples below relate dot pharmaceutical preparations.

Example A

Injection Vials

A solution of 100 g of a cylopeptide of the formula I and 5 g of disodium hydrogenphosphate in 3l of doubly distilled water is adjusted to pH 6.5 with 2 N hydrochloric acid, sterile filtered, filled into injection vials and lyophilized under sterile conditions, and the vials are sealed in a sterile manner. Each injection vial contains 5 mg of active compound.

Example B

Suppositories

A mixture of 20 g of active compound of the formula I is fused with 100 g of soya lecithin and 1400 g of cocoa butter, and the mixture is poured into moulds and allowed to cool. Each suppository contains 20 mg of active compound.

Example C

Solution

A solution of 1 g of active compound of the formula I, 9.38 g of NaH$_2$PO$_4$.2H$_2$O, 28.48 g of Na$_2$HPO$_4$.12H$_2$O and 0.1 g of benzalkonium chloride is prepared in 940 ml of doubly distilled water. The solution is adjusted to pH 6.8, made up to 1 l and sterilized by irradiation. This solution can be used in the form of eye drops.

Example D

Ointment 500 mg of active compound of the formula I are mixed with 99.5 g of petroleum jelly under aseptic conditions.

Example E

Tablets

A mixture of 100 g of a cyclopeptide of the formula I, 1 kg of lactose, 600 g of microcrystalline cellulose, 600 g of maize starch, 100 g of polyvinylpyrrolidone, 80 g of talc and 10 g of magnesium stearate is pressed to give tablets in a customary manner, such that each tablet contains 10 mg of active compound.

Example F

Coated Tablets

Tablets are pressed as stated in Example E and then coated in a customary manner with a coating of sucrose, maize starch, talc, tragacanth and colorant.

Example G

Capsules

Hard gelatin capsules are filled with an active compound of the formula I in the customary manner, so that each capsule contains 5 mg of active compound.

Example H

Inhalation Spray 14 g of active compound of the formula I are dissolved in 10 l of isotonic NaCl solution and the solution is filled into commercially available spray containers having a pump mechanism. The solution can be sprayed into the mouth or nose. One spray burst (about 0.1 ml) corresponds to a dose of about 0.14 mg.

The preceding examples can be repeated with similar success by substituted the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

---

---

What is claimed is:

1. A method for the prophylaxis or treatment of cardiac infarct, arterial sclerosis, apoplexy, angina pectoris, osteoporosis, angiogenesis, or restenosis after angioplasty, comprising administering a cyclopeptide compound of formula I $$\text{cyclo-(Arg-B-Asp-D-E)}$$

wherein

B is Gly, Ala, or —NH—Q—CO;

D is Nal, Phe, 4-Hal-Phe, or Phg;

E is Gly, Ala, Lys, Lys(Ac), Lys(AcNH$_2$), or Lys(AcSH);

Hal is F, Cl, Br, or I;

Q is alkylene having 1–6 C atoms; and

Ac is alkanoyl having 1–10 C atoms, or a physiologically acceptable salt thereof, with the proviso that said compound is not cyclo-(Arg-Gly-Asp-Phe-Val) or cyclo-(Arg-Ala-Asp-Phe-Val), in which optically active amino acids can be either the D or L form.

2. A method of claim 1, wherein said compound is administered in an amount of 0.01–2 mg/kg of body weight.

3. A method of claim 1, wherein said compound is:
   (a) cyclo-(Arg-Gly-Asp-D-Phe-Lys) or a physiologically acceptable salt thereof,
   (b) cyclo-(Arg-Gly-Asp-D-Phe-Gly) or a physiologically acceptable salt thereof.

4. A method of claim 3, wherein said compound is administered in an amount of 0.01–2 mg/kg of body weight.

5. A method of claim 1, wherein B is Gly, $-NH-(CH_2)_2-CO-$, $-NH-(CH_2)_3-CO-$, $-NH-(CH_2)_5-CO-$, or Ala.

6. A method of claim 1, wherein D is Phe or 4-Hal-Phe.

7. A method of claim 1, wherein D is D-Phe.

8. A method of claim 1, wherein B is Gly; D is D-Phe; and E is Lys, or Gly.

9. A method of claim 1, wherein B is Gly and D is D-Phe.

10. A method of claim 1, wherein E is Lys, Gly, or Lys(AcSH).

\* \* \* \* \*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 5 amino acids
      (B) TYPE: amino acid
      (D) TOPOLOGY: circular (ii) MOLECULE TYPE: peptide (xi) SEQUENCE DESCRIPTION: SEQ ID NO:1:

Arg Gly Asp Phe Gly
1               5

(2) INFORMATION FOR SEQ ID NO:2:

(i) SEQUENCE CHARACTERISTICS:
      (A) LENGTH: 5 amino acids
      (B) TYPE: amino acid
      (D) TOPOLOGY: circular (ii) MOLECULE TYPE: peptide (xi) SEQUENCE DESCRIPTION: SEQ ID NO:2:

Arg Gly Asp Phe Val
1               5